United States Patent
Stergiou et al.

(10) Patent No.: US 9,301,695 B2
(45) Date of Patent: Apr. 5, 2016

(54) STRESS MODEL BASED ON RR INTEGRAL AVERAGE

(71) Applicant: FUJITSU LIMITED, Kawasaki-shi, Kanagawa (JP)

(72) Inventors: Stergios Stergiou, East Palo Alto, CA (US); Jawahar Jain, Los Altos, CA (US); Shreyans Gandhi, Mumbai (IN); David L. Marvit, San Francisco, CA (US); Madan Bahadur, Mumbai (IN)

(73) Assignee: FUJITSU LIMITED, Kawasaki (JP)

( * ) Notice: Subject to any disclaimer, the term of this patent is extended or adjusted under 35 U.S.C. 154(b) by 597 days.

(21) Appl. No.: 13/745,099

(22) Filed: Jan. 18, 2013

(65) Prior Publication Data

US 2014/0206944 A1    Jul. 24, 2014

(51) Int. Cl.
*A61B 5/00* (2006.01)
*A61B 5/0205* (2006.01)
*A61B 5/024* (2006.01)

(52) U.S. Cl.
CPC ........... *A61B 5/0205* (2013.01); *A61B 5/02405* (2013.01)

(58) Field of Classification Search
CPC ..................... A61B 5/0205; A61B 5/02405
See application file for complete search history.

(56) References Cited

U.S. PATENT DOCUMENTS

2005/0154326 A1 *   7/2005   Martynenko et al. ......... 600/515

OTHER PUBLICATIONS

Litscher G et al., "Blue 405 nm laser light mediates heart rate—investigations at the acupoint Neiguan (Pe.6) in Chinese adults", North American Journal of Medical Sciences, 2009, vol. 1, No. 5, pp. 226-231.

* cited by examiner

*Primary Examiner* — George Manuel
(74) *Attorney, Agent, or Firm* — Maschoff Brennan

(57) ABSTRACT

A method of determining stress includes receiving a data signal including multiple consecutive RR intervals of a subject. The method may also include calculating heart rate variability (HRV) data for the subject from the data signal. The method may also include calculating an RR integral average (RRIA) from the HRV data, the RRIA indicating a stress level of the subject.

20 Claims, 8 Drawing Sheets

STRESS MODEL BASED ON RR INTEGRAL AVERAGE

FIELD

The embodiments discussed herein are related to determining stress based on an improved stress model that may include calculating a new parameter referred to herein as an RR integral average (RRIA).

BACKGROUND

Mental stress has been defined as "a real or perceived challenge, either endogenous or exogenous, that perturbs body equilibrium or 'homeostasis.' . . . . Whether the person can adapt to or cope with the stress will depend on the nature and severity of the stressor and the person's physical and mental state, which in turn depends on genetic, experiential, social, and environmental factors." See Welch, W. J., *Kidney Function* in Encyclopedia of Stress, 2007, Vol. 2.

Currently there is no reliable method to measure a person's mental stress. One common method that attempts to measure a person's stress is a psychological questionnaire. Some psychological questionnaires are relatively lengthy, requiring a half hour or more to complete. Thus, it is difficult to obtain real-time stress measurements based on questionnaires. Additionally, the filling out of the questionnaire by the person may create stress for the person. Given the time involved in completing the questionnaire and the potential to induce stress in the person, the results obtained by the questionnaire method may be delayed and/or may differ from actual stress which the person normally experiences.

Another method for measuring stress measures stress hormone levels in the blood, urine, or saliva of a person. Such stress hormone levels may become elevated when the person interprets a situation as being stressful. However, the measurement of stress hormones is invasive as it may require a blood, urine, or saliva sample of the person and additionally may be difficult or impossible to use for continuous monitoring.

The subject matter claimed herein is not limited to embodiments that solve any disadvantages or that operate only in environments such as those described above. Rather, this background is only provided to illustrate one example technology area where some embodiments described herein may be practiced.

SUMMARY

According to an aspect of an embodiment, a method of determining stress based on an RRIA includes receiving a data signal including multiple consecutive RR intervals of a subject. The method may also include calculating heart rate variability (HRV) data for the subject from the data signal. The method may also include calculating the RRIA from the HRV data, the RRIA indicating a stress level of the subject.

The object and advantages of the embodiments will be realized and achieved at least by the elements, features, and combinations particularly pointed out in the claims.

It is to be understood that both the foregoing general description and the following detailed description are exemplary and explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

Figure 1:
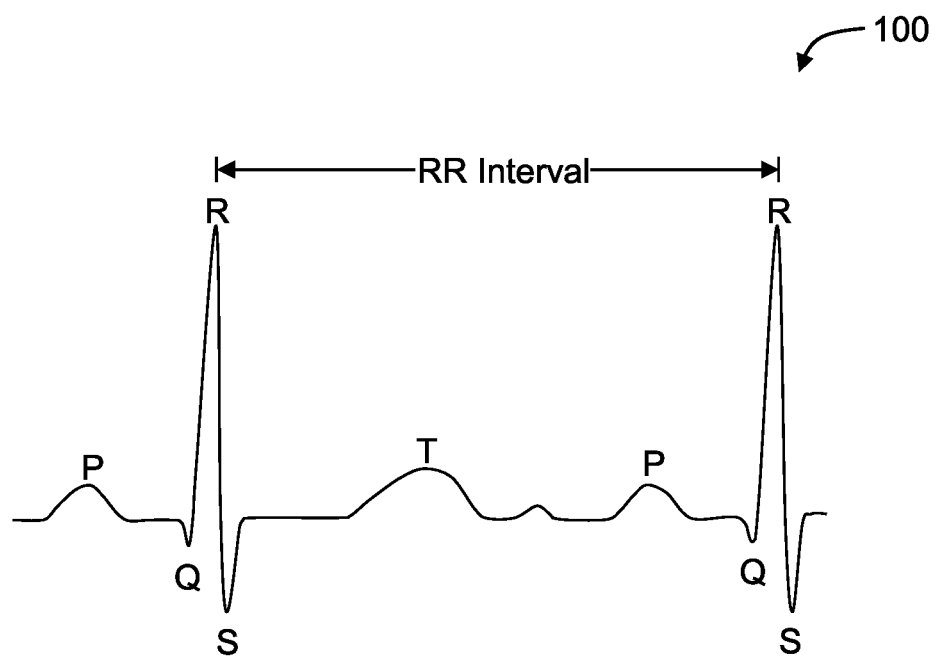
FIG. 1 is a graph including an example trace representing a normal heart rhythm.

Every person has an active sympathetic nervous system (SNS), which is responsible for inducing stress, and an active parasympathetic nervous system (PSNS), which is responsible for inducing relaxation. When a person is not stressed, the SNS and PSNS are in a healthy balance, which may be referred to as a baseline or non-stressed state. A person is considered stressed from a medical standpoint when stress hormones are being released over and above what is normal. The stress hormones are released from sympathetic nerves and adrenal glands and may include epinephrine, norepinephrine, and Cortisol, for example. When a person goes through stress, the sympathetic nerves and adrenal glands release such stress hormones.

Cortisol is produced by the adrenal gland in the zona fasciculata, the second of three layers comprising the outer adrenal cortex of the brain. The release of Cortisol is controlled by the hypothalamus, another part of the brain. The secretion of corticotropin-releasing hormone (CRH) by the hypothalamus triggers anterior pituitary secretion of adrenocorticotropic hormone (ACTH). ACTH is carried by the blood to the adrenal cortex, where it triggers glucocorticoid secretion. Its main functions in the body include increasing blood sugar through gluconeogenesis; suppressing the immune system; and aiding in fat, protein, and carbohydrate metabolism. CRH, ACTH and Cortisol are part of the limbic-hypothalamic-pituitary-adrenal (LHPA) axis and are relatively difficult to measure continuously and in real-time.

On the other hand, hormones such as epinephrine and norepinephrine are part of the sympathetic-adrenal-medullary (SAM) axis and may have a relatively immediate effect on various more measurable parameters. In particular, kidneys are rich in sympathetic nerves. When they release stress hormones such as norepinephrine, it then causes renal arteries to constrict. Constriction causes changes in blood flow. Some methods for determining stress detect stressed states generally based on changes in the blood flow through the renal arteries or through a single one of the renal arteries.

One method for determining stress that is accurate is the Doppler Resistive Index (RI) method. In the Doppler RI method, a Doppler ultrasound machine generates a velocity waveform of blood flow in the renal artery. The velocity indicated by the velocity waveform is proportional to the amount of renal blood flow. The RI may then be calculated form a peak value and a lowermost stable value (or trough) of the velocity waveform. A baseline Doppler RI measurement may be obtained when a subject is in a non-stressed state. Other Doppler RI measurements may be obtained, with any increase compared to the baseline Doppler RI measurement indicating that the subject is experiencing stress.

Another method for determining stress that has been validated by Applicants against the Doppler RI method may be variously referred to as the power spectrum method or the Doppler Fast Fourier Transform (FFT) method. Aspects of the power spectrum method are described in copending U.S. patent application Ser. No. 13/584,499, filed Aug. 13, 2012 and entitled FREQUENCY DOMAIN ANALYSIS TRANSFORM OF RENAL BLOOD FLOW DOPPLER SIGNAL TO DETERMINE STRESS LEVELS, which patent application is herein incorporated by reference. In the power spectrum method, a power spectrum may be calculated for the velocity waveform of the renal blood flow by, e.g., performing an FFT on the velocity waveform. The power spectrum, and/or a feature of the power spectrum such as a primary peak of the power spectrum, may indicate a stress level of the subject. Such power spectra may be obtained at various times. For example, a baseline power spectrum indicating a baseline stress level may be obtained when the subject is in a non-stressed state. Subsequently, a current power spectrum indicating a current stress level of the subject may be obtained and compared to the baseline power spectrum to determine a relative stress level of the subject. Both the Doppler RI method and the power spectrum method are referred to herein as renal blood flow methods since both are based on measurements of the renal blood flow of the subject. The renal blood flow methods are both examples of stress models.

Notwithstanding the accuracy of the renal blood flow methods, they are generally limited to use in environments where a Doppler ultrasound machine is available, e.g., typically in non-mobile clinical settings. Embodiments described herein, however, include stress determination methods and systems that may be practiced in mobile and/or non-mobile settings based on a new parameter referred to herein as an RR Integral Average (RRIA) that may be derived from data including multiple consecutive RR intervals for a subject.

Accordingly, an example system of determining stress based on the RRIA may include a cardiac sensor, such as a heart rate sensor, and a computing device such as a smartphone, a tablet computer, or a laptop computer. The cardiac sensor may be configured to generate a data signal including multiple consecutive RR intervals of a subject over time. The data signal generated by the cardiac sensor may include electrocardiography (ECG or EKG) data, for example.

The computing device may be configured to receive the data signal and to determine a length of each RR interval, where each RR interval corresponds to a heartbeat of the subject. The computing device may calculate a change in adjacent beat-to-beat intervals as the difference between each consecutive RR interval and an immediately preceding RR interval. The RRIA may then be calculated as the median of the changes in adjacent beat-to-beat intervals over a particular window, such as a time window, or the like, as described in more detail below. In some embodiments, each heartbeat may be sorted into a corresponding one of various "bins" based on a corresponding calculated change in adjacent beat-to-beat interval to generate a heart rate variability (HRV) histogram where the RRIA is the point in the HRV histogram which divides the HRV histogram into two equal areas. Optionally, the RRIA may be weighted with an average heart rate of the subject and/or with a root mean square of successive differences (RMSSD) of the consecutive RR intervals. Each of the various RRIA measures may be compared against a baseline measure for a given subject and/or against a median or average for multiple subjects.

The determination of stress based on the RRIA as summarized above and described in more detail below may generally be identified herein as the RRIA methods, all of which are examples of stress models. The determination of stress based primarily on the RRIA may be specifically identified herein as the first RRIA method or model. The determination of stress based on the RRIA weighted by the average heart rate may be specifically identified herein as the HR_RRIA method or model. The determination of stress based on the RRIA weighted by the average heart rate and the RMSSD may be specifically identified herein as the RMSSD_HR_RRIA method or model.

Embodiments of the present invention will be explained with reference to the accompanying drawings.

FIG. 1 is a graph including an example trace 100 representing a normal heart rhythm, arranged in accordance with at least some embodiments described herein. A cardiac sensor such as an ECG device may be configured to generate a data signal represented by such a trace by detecting electrical signals generated by the sinoatrial (SA) node of the heart, which electrical signals control the heart's rhythm.

The trace 100 includes various waves or portions labeled P, Q, R, S and T, some of which are sometimes grouped together and described as a complex, such as the QRS complex. In a normal heart rhythm, the SA node generates an electrical impulse which travels through the right and left atria. The P wave represents the electricity flowing through the atria. The QRS complex represents the flow through the ventricles as they contract to push the blood out from the heart. The T wave represents repolarization or the electrical resetting of the heart for the next beat. The next heart beat cycle begins at the next P wave.

As shown in FIG. 1, the RR interval is the time between successive R waves. Each RR interval corresponds to a heartbeat. Moreover, heart rate in terms of beats per minute is inversely proportional to the RR interval and may be calculated from the RR interval. Insofar as the length of each RR interval may vary from one heartbeat to the next, an instantaneous heart rate may be calculated for a single RR interval or an average heart rate may be calculated across multiple consecutive RR intervals. The variability of the RR interval from one heartbeat to the next is referred to as heart rate variability (HRV). The RRIA may be calculated from data representing the HRV (hereinafter "HRV data") as described in more detail below.

Figure 2:
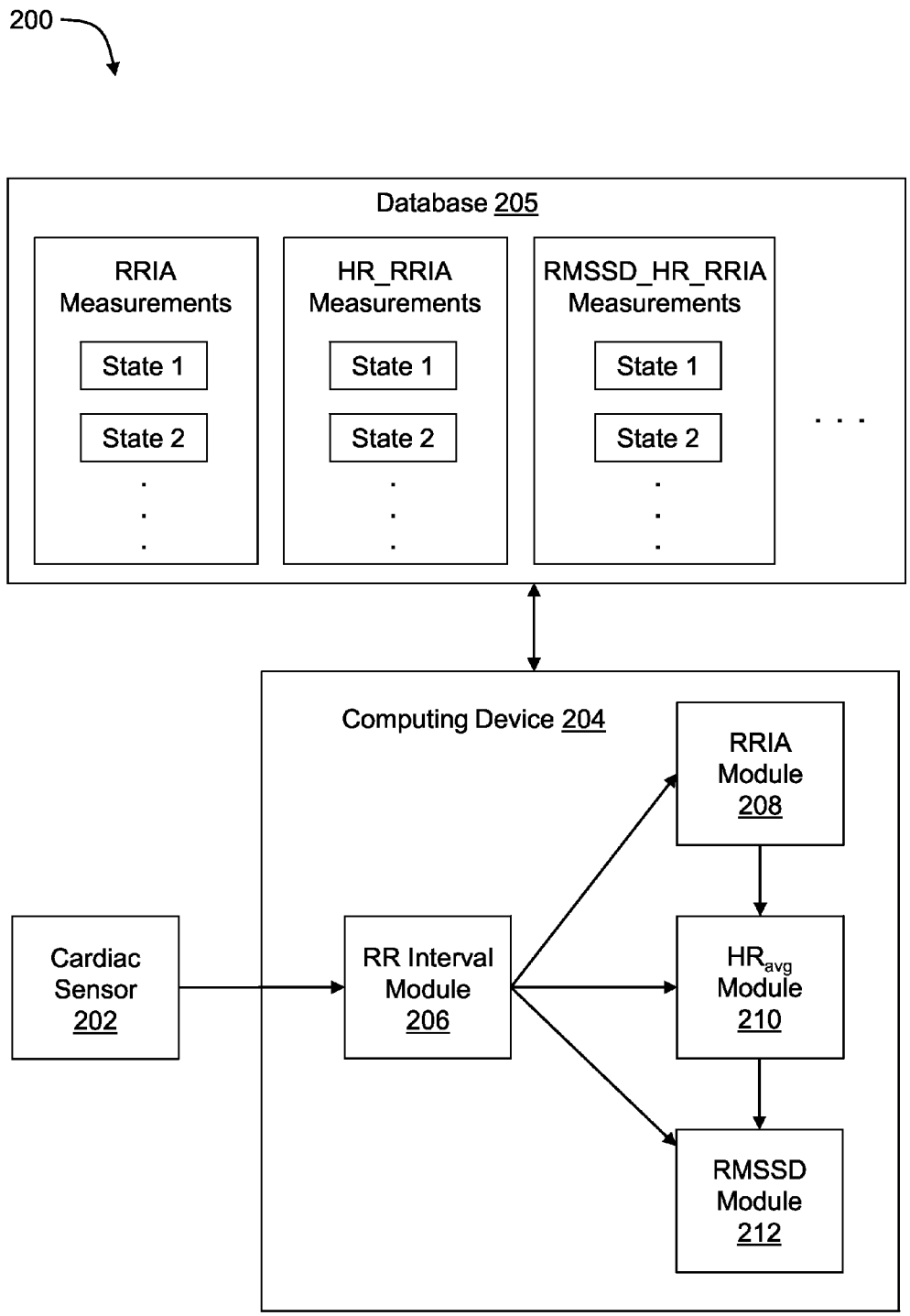
FIG. 2 is a block diagram of an example system of determining stress based on RRIA.

FIG. 2 is a block diagram of an example system 200 of determining stress based on RRIA, arranged in accordance with at least some embodiments described herein. The system 200 may include a cardiac sensor 202 and a computing device 204. In some embodiments, the system 200 may further include a database 205. Although not shown, the system 200 may optionally further include one or more batteries and/or other mobile power supplies configured to power the computing device 204 and/or the cardiac sensor 202. In these and other embodiments, the system 200 may be implemented as a mobile system. Accordingly, the computing device 204 may include, but is not limited to, a smartphone, a tablet computer, a laptop computer, or other mobile computing device, as well as traditionally non-mobile computing devices such as desktop computers.

With continued reference to FIG. 2, the cardiac sensor 204 may be configured to generate a data signal including multiple consecutive RR intervals of a subject. The data signal generated by the cardiac sensor 204 may be visually represented by an ECG trace, such as the trace 100 of FIG. 1, for example. The cardiac sensor 204 may include, but is not limited to, an ECG (or EKG) device, a pulse oximeter, a Holter monitor, a photoplethysmograph (PPG), a finger-attached, chest-strap, or ear-clip type heart rate monitor, or other suitable cardiac sensor.

The computing device 204 may be communicatively coupled to the cardiac sensor 202 via a wired or wireless connection. The computing device 204 may be configured to receive the data signal generated by the cardiac sensor 202. The computing device 204 may additionally be configured to determine stress based on RRIA. In some embodiments, for example, the computing device 204 may be configured to calculate HRV data for the subject from the data signal and may be further configured to calculate the RRIA from the HRV data, the RRIA indicating the stress level of the subject.

Accordingly, the computing device 204 may include an RR interval module 206 and an RRIA module 208. Although not required, the computing device 204 may additionally include an average heart rate ($HR_{avg}$) module 210, and/or an RMSSD module 212. The RR interval module 206, the RRIA module 208, the $HR_{avg}$ module 210 and the RMSSD module 212 may be implemented in software, hardware, or a combination thereof. When implemented at least partially in software, the computing device 204 may additionally include a memory and a processing device configured to execute computer instructions stored in the memory to cause the computing device 204, and more particularly the processing device, to perform the operations described with respect to the various modules 206, 208, 210, and/or 212.

In general, the RR interval module 206 may be configured to receive the data signal generated by the cardiac sensor 202, the data signal including the multiple consecutive RR intervals. The RR interval module 206 may be further configured to calculate a length of time of each of the consecutive RR intervals from the data signal. Each RR interval may represent or correspond to a heartbeat.

The RRIA module 208 may be configured to receive the calculated lengths of time of the RR intervals from the RR interval module 206. The RRIA module 208 may be further configured to calculate HRV data for the subject from the calculated lengths of time of the RR intervals. Calculating the HRV data may include calculating a change in adjacent beat-to-beat intervals as a difference, or more particularly as an absolute value of a difference, between each consecutive RR interval and an immediately preceding RR interval.

In other embodiments, the RRIA module 208 may be configured to calculate HRV data in some other manner. For instance, the RRIA module 208 may be configured to calculate the HRV data as a difference between an average RR interval in adjacent respiratory cycles and/or in some other manner.

The RRIA may then be calculated by the RRIA module 208 from the HRV data. For example, the RRIA may be calculated as the median of the differences between each consecutive RR interval and the immediately preceding RR interval over a particular window. In some embodiments, the HRV data may include an HRV histogram where each heartbeat may be sorted into a corresponding one of various "bins" based on a corresponding calculated difference between the consecutive RR interval and the immediately preceding RR interval. In these and other embodiments, the RRIA module 208 may calculate the RRIA as a point in the HRV histogram which divides the HRV histogram into two equal areas, or more particularly according to equation 1:

$$\int_0^{RRIA} f(x)dx = \int_{RRIA}^{\infty} f(x)dx \quad \text{(Equation 1)},$$

where f(x) represents the HRV histogram.

Briefly, the database 205 may include stress measurements such as RRIA-based measurements and/or other stress measurements for multiple subjects. Additional details regarding the database 205 are provided below.

Figure 3:
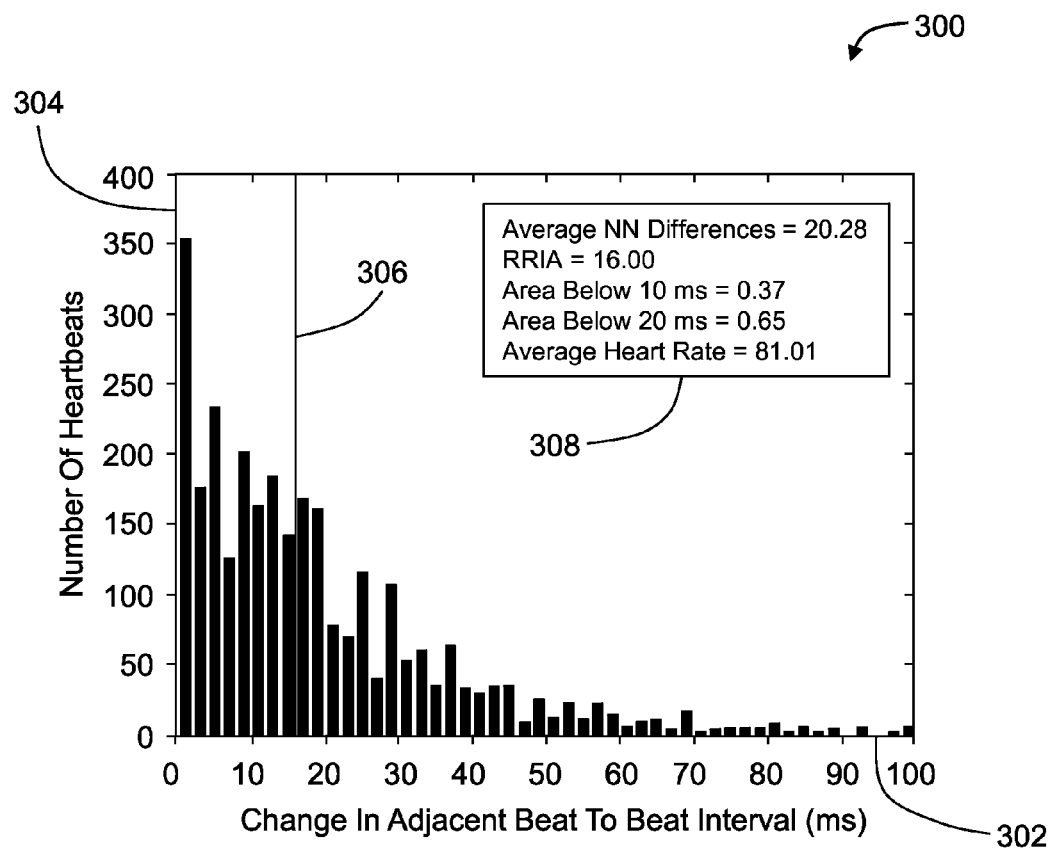
FIG. 3 is a graph including an example HRV histogram.

FIG. 3 is a graph 300 including an example HRV histogram, arranged in accordance with at least some embodiments described herein. In the graph 300 of FIG. 3, the horizontal axis 302 is divided into bins corresponding to changes in adjacent beat-to-beat intervals (in units of milliseconds (ms)) and the vertical axis 304 corresponds to the number of heartbeats sorted into the respective bins. Each of the bins is 2 ms wide in the illustrated embodiment, but the bins may more generally have any desired width.

In the example of FIG. 3, the RRIA is calculated to be sixteen. In particular, the value of sixteen along the horizontal axis is the point in the HRV histogram of FIG. 3 which divides the HRV histogram into two substantially equal areas in the illustrated example. Thus, a portion of the HRV histogram to the left of a reference line 306 (aligned at sixteen on the horizontal axis 302) has an area that is equal to an area of a portion of the HRV histogram to the right of the reference line 306.

The graph 300 of FIG. 3 additionally includes a box 308 with information about the HRV histogram. The box 308 identifies the "Average NN Differences" for the HRV histogram of FIG. 3, where the abbreviation "NN" stands for normal-to-normal intervals, i.e., intervals between consecutive QRS complexes resulting from sinus node de-polarizations. In practice, RR and NN intervals usually appear to be the same. In addition to identifying the "Average NN Differences" for the HRV histogram of FIG. 3, the box 308 identifies the corresponding RRIA, a normalized "Area Below 10 ms", a normalized "Area Below 20 ms", and an "Average Heart Rate."

Returning to FIG. 2, the RRIA may be calculated by the RRIA module 208 over a time window having a predetermined length $\Delta t$, such as about 120 seconds or any other suitable length of time. The time window may be a shifting time window. For example, the time window may end at a current time (or more generally at an end time) and begin at the current time minus the predetermined length $\Delta t$ (or more generally at a begin time equal to the end time minus the predetermined length $\Delta t$). Thus, as time progresses and the time window shifts, sorted heartbeats corresponding to RR intervals acquired outside the time window may be discarded and an updated RRIA calculation may be performed. Alternately, the window may be defined as a fixed number of RR or NN intervals, such as the most recent 120 RR or NN intervals or some other fixed number of RR or NN intervals.

The calculated RRIA generated by the RRIA module 208 may be used by itself as an indicator of the stress level of the subject. Alternately or additionally, other factors may be taken into account. For example, the RRIA may be weighted by the average heart rate of the subject and/or by the RMSSD of the HRV data. In these and other embodiments, the $HR_{avg}$ module 210 may be configured to calculate a heart rate-weighted RRIA (referred to hereinafter as HR_RRIA) and/or the RMSSD module 212 may be configured to calculate an RMSSD-weighted HR_RRIA (referred to hereinafter as RMSSD_HR_RRIA).

It is understood that the same HRV may be obtained under the same conditions at both a first average heart rate, say 70 beats per minute (bpm), and at a second average heart rate, say 100 bpm. Since higher HR is known to indicate higher stress, the HRV with the second average heart rate of 100 bpm is more likely to represent stress than the first average heart rate of 70 bpm. The RRIA may be weighted by the average heart rate to account for the foregoing.

Accordingly, the $HR_{avg}$ module 210 may be configured to determine, from the RR intervals calculated by the RR interval module 206, an average heart rate of the subject. For example, the $HR_{avg}$ module 210 may determine an instantaneous heart rate for each of multiple consecutive RR intervals and may then calculate an average of the resulting instantaneous heart rates to obtain the average heart rate, or the $HR_{avg}$ module 210 may determine an average RR interval over multiple consecutive RR intervals and may then calculate the average heart rate from the average RR interval, or the $HR_{avg}$ module 210 may determine the average heart of the subject in some other manner. Alternately or additionally, a filter may be applied to the underlying data so that heart rate calculations from noisy data do not corrupt the stress determinations.

The average heart rate may be determined over a time window having a predetermined length Δt, such as about 120 seconds or any other suitable length of time. Alternately or additionally, the average heart rate may be determined over a same time window as the RRIA. The time window may be a shifting time window that is shifted constantly or periodically. For constant shifting, the time window may end at a current time and begin at the current time minus the predetermined length Δt. For periodic shifting, the time window may be shifted periodically, such as every 30 seconds or any other suitable length of time. In both cases, as time progresses, RR intervals acquired outside the time window may be discarded and an updated average heart rate may be determined. In an example embodiment, the average heart rate may be determined over a time window of 120 seconds that is shifted every 30 seconds.

Finally, the HR_RRIA may be calculated by the average HR module 210 according to equation 2:

$$HR\_RRIA = (RRIA/HR_{avg})*C1 \qquad \text{(Equation 2)},$$

where RRIA is the RRIA calculated by the RRIA Module 208, $HR_{avg}$ is the average heart rate determined by the $HR_{avg}$ module 210, and C1 is a constant.

As already mentioned, the average heart rate $HR_{avg}$ may be determined by the $HR_{avg}$ module 210 by determining an instantaneous heart rate for each of multiple consecutive RR intervals and then calculating an average of the resulting instantaneous heart rates to obtain the average heart rate $HR_{avg}$, or by determining an average RR interval over multiple consecutive RR intervals and then calculating the average heart rate from the average RR interval, or in some other manner.

The constant C1 may serve as a normalization factor in some embodiments. For example, the constant C1 may be equal to a normalization C(RRIA) of the RRIA multiplied by a normalization C(HR) of the average heart rate $HR_{avg}$, or C1=C(RRIA)*C(HR). Alternately or additionally, the constant C1 may be user-specific and/or may change based upon the standard deviation. The constant C1 may be 60 in some embodiments. Moreover, because the RRIA is an inverse marker of stress as described with respect to FIGS. 4A-4B, and because the HR_RRIA directly depends on the RRIA, the HR_RRIA is also an inverse marker of stress.

The RMSSD module 212 may be configured to take the shape of the HRV histogram into account when determining stress levels by calculating the RMSSD_HR_RRIA. Regarding HRV histogram shape, two distributions may have the same RRIA while one of the distributions contains more cases of very low HRV (e.g., more cases of changes in adjacent beat-to-beat intervals of less than about 10 ms) than the other distribution. For instance, a first one of the distributions may have changes in beat-to-beat intervals of 19, 20, 20, 20 and 21 while the second of the distributions may have changes in beat-to-beat intervals of 5, 5, 20, 20 and 21. In the foregoing example, each of the distributions may have a same RRIA of 20. However, since lower HRV is known to indicate higher stress, the second distribution with intervals of 5, 5, 20, 20 and 21 may be more likely to represent stress than the first distribution with intervals of 19, 20, 20, 20 and 21.

One way to describe the shape of the HRV histogram is in terms of the RMSSD of the HRV histogram. Alternately or additionally, a standard deviation of the HRV histogram may be used. The RMSSD may be calculated according to equation 3:

$$RMSSD = \{[\Sigma(RR_{i+1}-RR_i)^2]/n\}^{1/2} \qquad \text{(Equation 3)},$$

where $RR_{i+1}$ is a consecutive $(i+1)^{th}$ RR interval, $RR_i$ is an immediately preceding $i^{th}$ RR interval, and n is the total number of RR intervals taken in the calculation of RMSSD. In some embodiments, the RR intervals taken in the calculation of the RMSSD may include the RR intervals from the time window for which RRIA is calculated. Alternately or additionally, the RMSSD may be filtered.

Finally, the RMSSD_HR_RRIA may be calculated by the RMSSD module 212 according to equation 4:

$$RMSSD\_HR\_RRIA = HR\_RRIA * RMSSD/C2 \qquad \text{(Equation 4)},$$

where C2 is a constant.

The constant C2 may serve as a normalization factor in some embodiments. For example, the constant C2 may be equal to a normalization C(RMSSD) of the RMSSD multiplied by the constant C1, or C2=C(RMSSD)*C1. Alternately or additionally, the constant C2 may be user-specific and/or may change based upon the standard deviation. The constant C2 may be 10 in some embodiments.

Equation 4 effectively scales the HR_RRIA by the RMSSD over the same time window as the HR_RRIA and captures changes happening in the HRV histogram which are not reflected in the RRIA. Moreover, because the RMSSD_HR_RRIA directly depends on the HH_RRIA, the RMSSD_HR_RRIA is also in inverse marker of stress.

The above-described RRIA-based measurements (e.g., RRIA, HR_RRIA, and RMSSD_HR_RRIA measurements) are examples of stress measurements. These and other stress measurements are relative measurements and are often compared to a reference. For example, a stress measurement for a subject may be compared to a baseline stress measurement for the same subject, such as described in further detail below with respect to FIGS. 4A-4B.

Alternately or additionally, the stress measurement for the subject may be compared to an average or median value of stress measurements for multiple subjects. Accordingly, and as illustrated in FIG. 2, the system 200 may include the database 205. In general, the database 205 may include stress measurements for one or more different stress models. For example, the database 205 is illustrated with stress measurements for three different stress models, including "RRIA Measurements" for the first RRIA model, "HR_RRIA Measurements" for the HR_RRIA model, and "RMSSD_HR_RRIA Measurements" for the RMSSD_HR_RRIA model. Measurements for other stress models may alternately or additionally be included in the database 205, and/or stress measurements for more or fewer than three stress models may be included in the database 205.

FIG. 2 further discloses that the measurements for each of the stress models may be divided into different states, such as "State 1", "State 2", and so on. The different states generally refer to a stress state of the subjects when the corresponding measurements are obtained. For instance, "State 1" may refer to a stress state in which each of the subjects is exposed to the same first stress event, "State 2" may refer to a stress state in which each of the subjects is exposed to the same second stress event, and so on. Examples of stress events include relaxation, being administered an examination, being informed of an upcoming procedure (such as a pin prick), being subject to the procedure, sleeping, walking or running a predetermined distance or time, deep breathing for a predetermined time, meditating for a predetermined time, or the like or any combination thereof.

A median or average for the measurements in each state may be included in the database 205 and/or may be derived from the measurements in the database 205. Accordingly, a stress measurement—or stress level—for a subject may be obtained according to one or more of the stress models while the subject is in a particular stress state. The stress measurement may then be compared to the median or average for the corresponding stress model and state to determine, e.g., whether the subject's measurement is above or below the median or average. If the subject's measurement indicates that the subject is significantly more stressed than his cohorts, as determined by comparison to the median or average, a treatment can be identified and prescribed to the subject to improve the subject's stress level.

Alternately or additionally, stress measurements for the subject may be obtained according to multiple different stress models. Each stress measurement may be compared to the corresponding median or average from the database 205. In this manner, multiple different stress models may be used to cross-check each other and determine a validity and/or acuteness of the subject's stress level.

Optionally, the database 205 may further include additional data about the subjects from which the measurements are obtained, such as age, height, weight, body mass index (BMI), gender, medical conditions, or the like or any combination thereof. The additional data may be associated with the measurements. In these and other embodiments, the median or average may be refined according to any of age, height, weight, BMI, gender, medical conditions, or the like. Thus, a stress measurement for a subject of a particular age, height, weight, BMI, gender, and/or medical condition may be compared to a median or average of stress measurements for subjects with similar age, height, weight, BMI, gender, and/or medical conditions.

Alternately or additionally, the database 205 may further include additional measurements for the subjects obtained at the same time or around the same time as the stress measurements. The additional measurements may include heart rate, breathing rate, or the like or any combination thereof.

In some embodiments, the acuteness or even the validity of the stress measurements may be cross-checked by looking at orthogonal measurements, such as heart rate, breathing rate, or the like. For example, suppose an RRIA measurement for a subject (and/or a measurement(s) for a different stress model(s)) indicates that the subject is stressed based on a comparison to the corresponding median or average obtained from the database 205. By also looking at the heart rate for the subject or another orthogonal measurement, it may be possible to, e.g., confirm that the subject is stressed, identify how acute the stress is, and/or determine that the subject is not stressed. For instance, if the subject's heart rate compared to the median or average heart rate is lower than the other subjects in the same state, it may be determined that the stress measurements for the subject are invalid, or that the stress level of the subject is not very acute.

In these and other embodiments, the computing device 204 may communicate with the database 205 to compare the RRIA-based stress measurements it calculates against corresponding medians or averages. Alternately or additionally, prior to the comparison, the computing device 204 may first communicate with the database 205 and access the data therein to determine the median or average. As suggested by the preceding discussion, the criteria considered in determining the median or average, whether by the computing device 204 or some other device, may include at least the stress model and the state as well as one or more of: age, height, weight, BMI, gender, and/or medical conditions of the subject. Alternately or additionally, stress measurements obtained by the computing device 204 may be saved to the database 205.

Figure 4A:
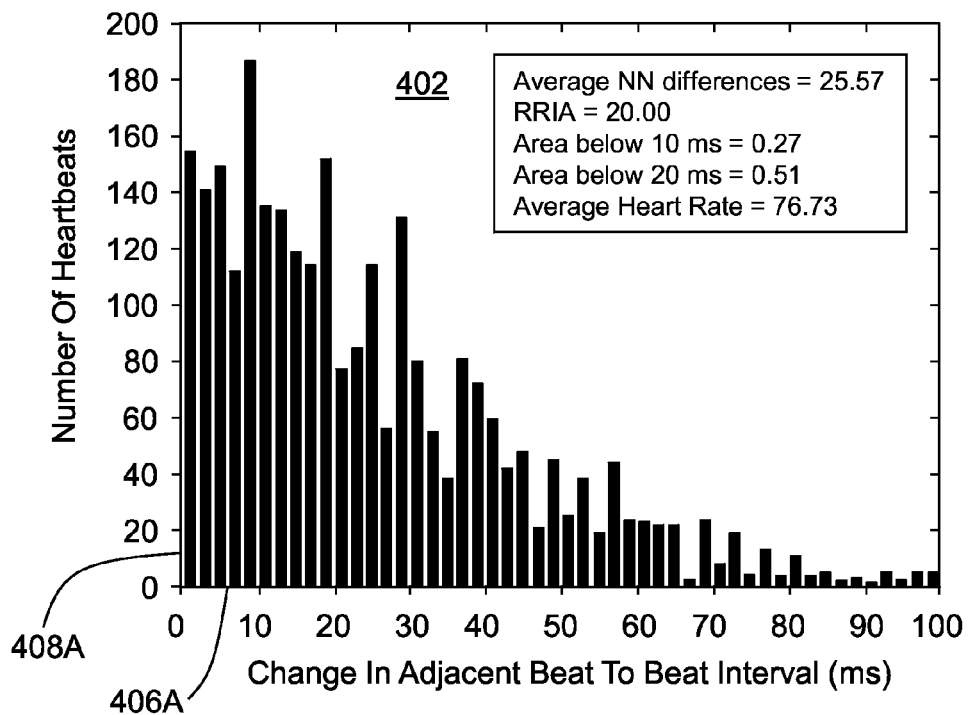
FIGS. 4A and 4B respectively illustrate graphs including HRV histograms corresponding to a non-stressed state and a stressed state for the same subject.
Figure 4B:
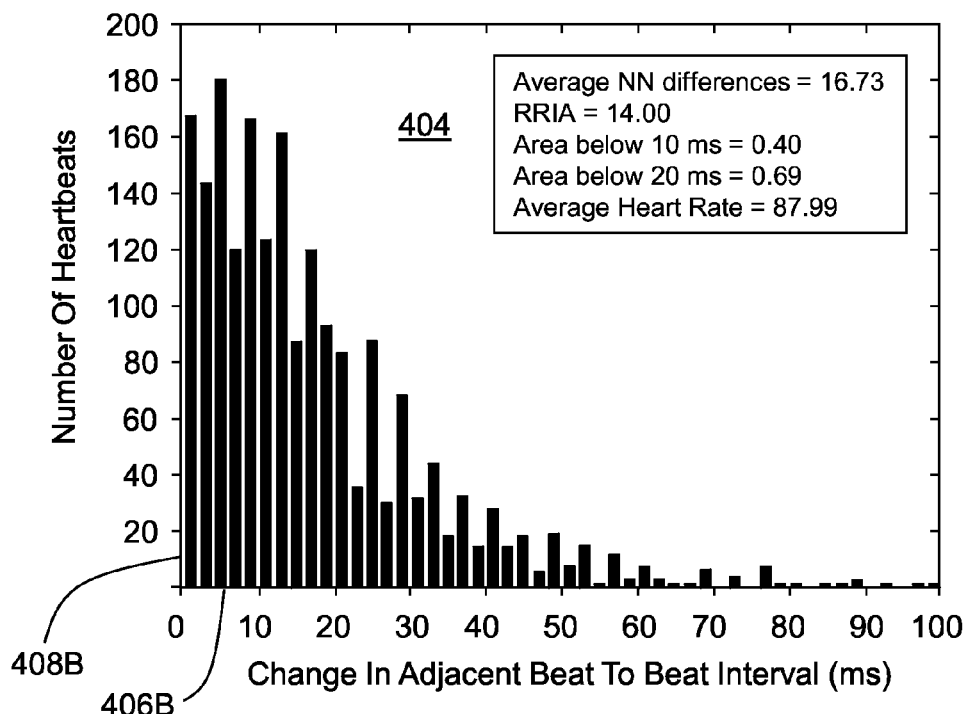

FIGS. 4A and 4B respectively illustrate graphs 402 and 404 including HRV histograms corresponding to a non-stressed state and a stressed state for the same subject, arranged in accordance with at least some embodiments described herein. The stressed state may correspond to a first stress state, while the non-stressed state may correspond to a second stress state; the first and second stress states may each be any of the stress states such as described above. As in FIG. 3, in each of FIGS. 4A and 4B, the horizontal axis 406A, 406B is divided into bins corresponding to changes in adjacent beat-to-beat intervals and the vertical axis 408A, 408B corresponds to the number of heartbeats sorted into the respective bins. Each of the bins is 2 ms wide in the illustrated embodiment, but the bins may more generally have any desired width.

There is a visible left shift from the non-stressed state of FIG. 4A to the stressed state of FIG. 4B. In particular, as compared to the non-stressed state of FIG. 4A, in the stressed state of FIG. 4B, the relative areas below both 10 ms and 20 ms have increased (e.g., shifted to the left), leading to a corresponding decrease or left-shift in the RRIA from the non-stressed state of FIG. 4A to the stressed state of FIG. 4B. Indeed, in the example of FIGS. 4A-4B, the RRIA changes from 20.00 in the non-stressed state to 14.00 in the stressed state. Accordingly, RRIA is an inverse marker of stress insofar as the RRIA decreases with an increase in stress. Either or both of the RRIAs of FIGS. 4A and 4B may be weighted by one or more of the subject's average heart rate and/or the RMSSD of the corresponding RR intervals.

The left shift in the HRV histogram of the same subject from the non-stressed state of FIG. 4A to the stressed state of FIG. 4B may be explained as follows. When a subject is stressed, the sympathetic cardiac control may increase (associated with the fight or flight response), or the parasympathetic control (associated with relaxation, rest and digest processes) may decrease, or both. The foregoing may lead to the disturbance of the balance between sympathetic and parasympathetic control. The imbalance causes the decreased HRV, leading to the increased frequency of the low RR interval differences, which is reflected as the left shift in the HRV histogram.

Each of the RRIA methods—including the first RRIA method, the HR_RRIA method and the RMSSD_HR_RRIA method—has been validated by Applicants against one or both of the renal blood flow methods. For example, in one study, the Doppler RI method was implemented to determine the stress level of 13 subjects in various stress states. In addition to monitoring renal blood flow for determining stress levels according to the Doppler RI method, the subjects' heart rate was simultaneously monitored for determining stress levels according to the RRIA methods as well as for a method known as the LF/HF method (described below).

A baseline stress level (or measurement), a first stress level (or measurement), and a second stress level (or measurement) were determined for each of the subjects according to the Doppler RI method, the RRIA methods, and the LF/HF method while each of the subjects was in a respective one of three different states. The baseline stress level was obtained when each of the subjects was in a non-stressed state. The first stress level was induced by the administration of an examination consisting of arithmetic and logic questions with a strict time limit for answering each question. The questions were designed such that they were easy to understand but difficult to solve in the given time. The second stress level was induced by indicating to each subject that a blood sample was needed by application of a pin prick, but the pin prick was never actually applied.

Figure 5:
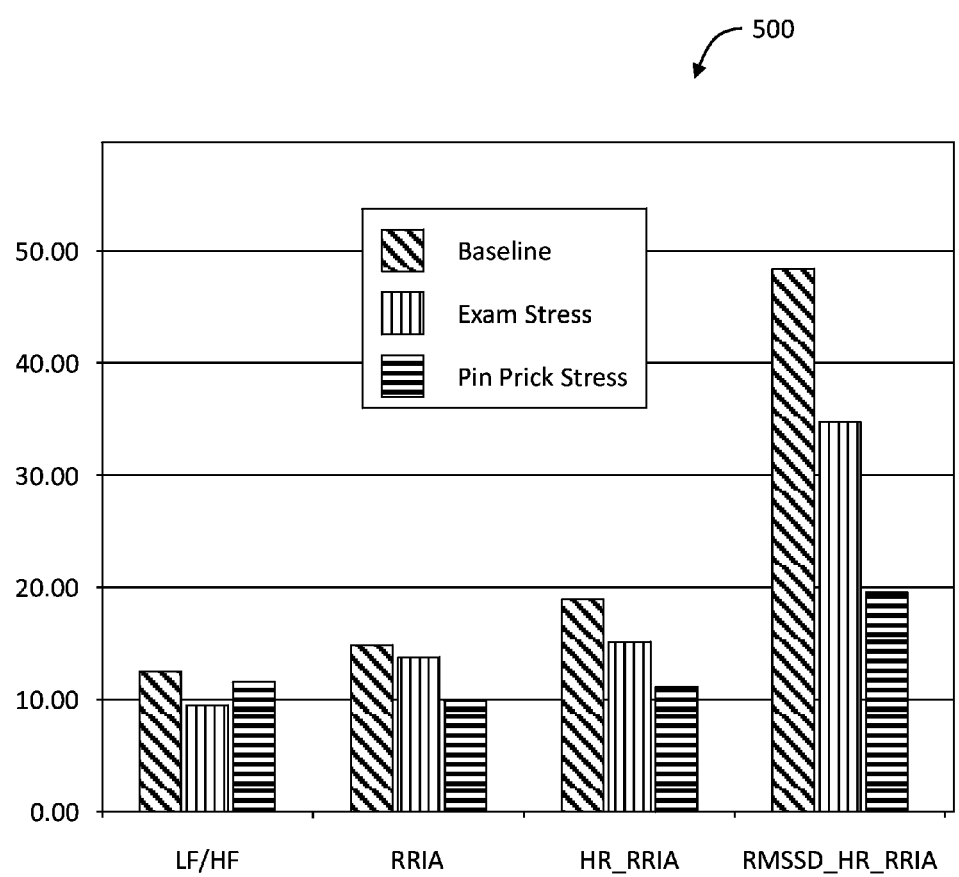
FIG. 5 is a graph illustrating summary results of a study in which stress levels were determined for various subjects in each of three different states using various methods.

FIG. 5 is a graph 500 illustrating summary results of the foregoing study in which stress levels (or measurements) were determined for various subjects in the three different states using the RRIA methods and the LF/HF method, arranged in accordance with at least some embodiments described herein. The stress levels determined according to the Doppler RI method are not illustrated, but confirmed that each of the subjects was more stressed at their respective first stress level than at their respective baseline level and that a majority of the subjects were more stressed at their respective second stress level than at their respective first stress level.

As already mentioned above, each of the RRIA, HR_RRIA and RMSSD_HR_RRIA markers is an inverse marker of stress level. Accordingly, the results of FIG. 5 illustrate the agreement of the RRIA methods with the Doppler RI method. Namely, for each of the RRIA methods, there is a decrease in the respective marker from the baseline level ("Baseline" in FIG. 5) to the first stress level ("Exam Stress" in FIG. 5) corresponding to a relative increase in stress level, which agrees with the Doppler RI method. There is also a decrease in the respective marker from the first stress level to the second stress level ("Pin Prick Stress" in FIG. 5) similarly corresponding to a relative increase in stress level, which also agrees with the Doppler RI method.

The stress level determinations according to the LF/HF method, however, did not fully agree with the stress level determinations according to the Doppler RI method. Briefly, the LF/HF method involves analysis of a subject's HRV. The HRV analysis may be carried out in the frequency domain or the time domain. In the frequency domain analysis, a frequency transform of a heart rate waveform of the subject is taken and frequency bands are defined for very low frequency (VLF) regions, low frequency (LF) regions and high frequency (HF) regions. In theory, the power of the spectrum in these regions may depend on stress such that a LF/HF power ratio may be taken as a stress level of the subject. In the time domain analysis, the heart rate change in subsequent heart beats is basically correlated with the stress.

Figure 6A:
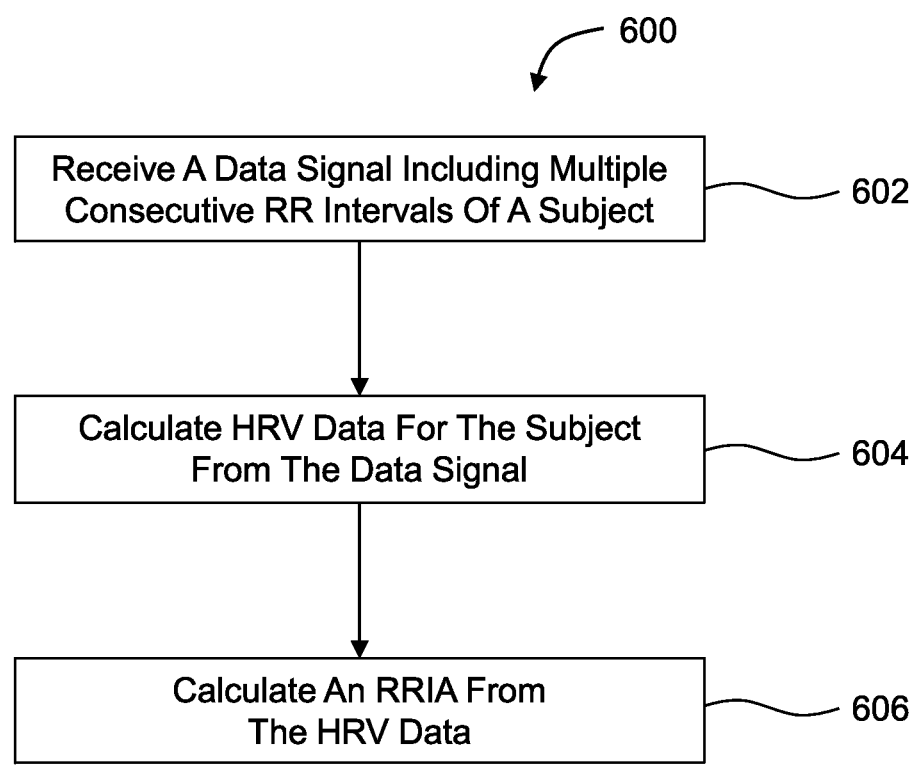
FIG. 6A shows an example flow diagram of a method of determining stress based on RRIA.

FIG. 6A shows an example flow diagram of a method 600 of determining stress based on RRIA, arranged in accordance with at least some embodiments described herein. The method 600 and/or variations thereof may be implemented, in whole or in part, by a system, such as the system 200 of FIG. 2. Alternately or additionally, the method 600 and/or variations thereof may be implemented, in whole or in part, by a processor or other processing device. Although illustrated as discrete blocks, various blocks may be divided into additional blocks, combined into fewer blocks, or eliminated, depending on the desired implementation.

The method 600 may begin at block 602 in which a data signal including multiple consecutive RR intervals of a subject is received. For example, such a data signal may be received by the computing device 204 from the cardiac sensor 202 of FIG. 2.

In block 604, HRV data for the subject may be calculated from the data signal. The HRV data may include multiple differences, e.g., each difference may include a difference between a given one of the multiple consecutive RR intervals and an immediately preceding RR interval.

In block 606, the RRIA may be calculated from the HRV data, the RRIA indicating a stress level of the subject. In some embodiments, calculating the RRIA from the HRV data may include calculating a median of the differences included in the HRV data.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

In some embodiments, the HRV data includes an HRV histogram and calculating the RRIA includes calculating a point in the HRV histogram which divides the HRV histogram into two equal or substantially equal areas. Alternately or additionally, calculating the RRIA from the HRV data may include calculating the RRIA according to equation 1 above.

Optionally, the method 600 may further include weighting the RRIA with at least one of the average heart rate of the subject or the RMSSD of the multiple consecutive RR intervals. The RMSSD may be calculated according to equation 3 above. Weighting the RRIA may include calculating the HR_RRIA according to equation 2 above. Alternately or additionally, weighting the RRIA may include calculating the RMSSD_HR_RRIA according to equation 4 above.

Alternately or additionally, the stress level may be determined at multiple different times. In this and other examples, the data signal may include a first data signal generated when the subject is in a non-stressed state, the HRV data may include first HRV data, and the RRIA may include a first RRIA representing a baseline stress level of the subject. Accordingly, the method 600 may further include assessing a current stress level of the subject by receiving a second data signal including multiple consecutive RR intervals of the subject at a current time. Second HRV data may be calculated for the subject from the second data signal as explained above. A second RRIA may be calculated from the second HRV data, the second RRIA indicating a current stress level of the subject. The first RRIA or a first value derived therefrom (e.g., HR_RRIA or RMSSD_HR_RRIA), respectively, may be compared to the second RRIA or a second value derived therefrom (e.g., also HR_RRIA or RMSSD_HR_RRIA) and it may be determined whether the subject is in a stressed state based on the comparison.

Determining whether the subject is in a stressed state based on the comparison may include determining that the subject is in a stressed state at the current time when the second RRIA or the second value, respectively, is less than the first RRIA or the first value, or determining that the subject is in a non-stressed state at the current time when the second RRIA or the second value, respectively, is greater than the first RRIA or the first value.

In some embodiments, the method 600 may further include recommending a stress-reduction treatment for the subject to reduce the current stress level in response to determining that the subject is in a stressed state at the current time. The stress reduction treatment may include medication, counseling, meditation, one or more mental or physical exercises, or postponement of an imminent medical procedure, or the like or any combination thereof.

Alternately or additionally, the method 600 may further include comparing the RRIA to a first median of multiple RRIAs for multiple subjects, each of the RRIAs corresponding to a different one of the subjects, or comparing a first value derived from the first RRIA to a second median of multiple second values derived from the RRIAs, each of the second values corresponding to a different one of the RRIAs. For example, the RRIA, HR_RRIA, or RMSSD_HR_RRIA may be compared, respectively, to a median of RRIAs, a median of HR_RRIAs, or a median of RMSSD_HR_RRIAs. In these and other embodiments, the method 600 may further include determining whether the subject is in a stressed state based on the comparison. For example, it may be determined that the subject is in a stressed state when the RRIA or the first value, respectively, is less than the first median or the second median. Alternately, it may be determined that the subject is in a non-stressed state when the RRIA or the first value, respectively, is greater than the first median or the second median.

Figure 6B:
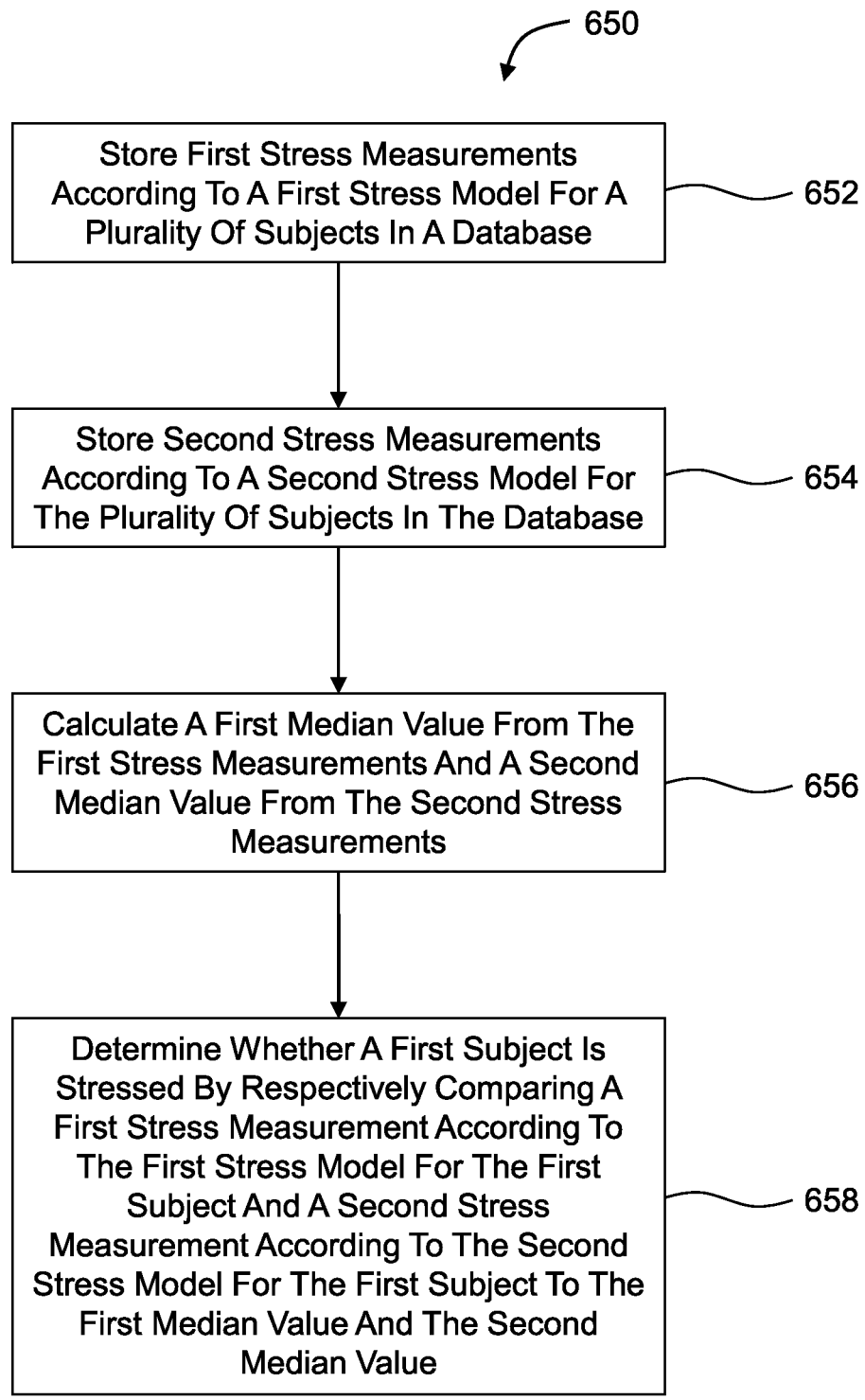
FIG. 6B shows an example flow diagram of another method of determining stress.

FIG. 6B shows an example flow diagram of another method 650 of determining stress, arranged in accordance with at least some embodiments described herein. The method 650 and/or variations thereof may be implemented, in whole or in part, by a system, such as the system 200 of FIG. 2. Alternately or additionally, the method 650 and/or variations thereof may be implemented, in whole or in part, by a processor or other processing device. Although illustrated as discrete blocks, various blocks may be divided into additional blocks, combined into fewer blocks, or eliminated, depending on the desired implementation.

The method may begin at block 652 in which first stress measurements according to a first stress model for multiple subjects are stored in a database. The first stress model may include one of the RRIA methods, one of the renal blood flow methods, or the like. Accordingly, the first stress measurements may include RRIA measurements, HR_RRIA measurements, RMSSD_HR_RRIA measurements, Doppler RI measurements, power spectrum measurements, or the like.

In block 654, second stress measurements according to a second stress model for the subjects are also stored in the database. Similar to the first stress model, the second stress model may include one of the RRIA methods, one of the renal blood flow methods, or the like, such that the second stress measurements may similarly include RRIA measurements, HR_RRIA measurements, RMSSD HR_RRIA measurements, Doppler RI measurements, power spectrum measurements, or the like. The second stress model and the first stress model may be different stress models. The database referenced in blocks 652 and 654 may include the database 205 of FIG. 5, for instance.

In block 656, a first median value is calculated from the first stress measurements and a second median value is calculated from the second stress measurements. Each of the first and second median value may include a different one of a median RRIA, a median HR_RRIA, a median RMSSD HR_RRIA, a median Doppler RI, a median power spectrum value, or the like.

In block 658, it is determined whether a first subject is stressed by respectively comparing a first stress measurement according to the first stress model for the first subject and a second stress measurement according to the second stress model for the first subject to the first median value and the second median value.

In some embodiments, the first stress measurements and the second stress measurements include, for each of the subjects, a measurement according to the corresponding stress model for the corresponding subject in each of multiple different states. The measurements for each state may be grouped or otherwise associated together as illustrated in FIG. 2. The first median value may be calculated from the first stress measurements for a single one of the different stress states. Analogously, the second median value may be calculated from the second stress measurements for a single one of the different stress states.

In these and other embodiments, the method 650 may further include calculating multiple different third median values from the first stress measurements for different ones of the multiple different stress states. The third median values may include, for example, a median of the first stress measurements for a first stress state, a median of the first stress measurements for a second stress state, and so on. Analogously, the method 650 may further include calculating multiple different fourth median values from the second stress measurements for different ones of the multiple different stress states. The fourth median values may include, for example, a median of the second stress measurements for a first stress state, a median of the second stress measurements for a second stress state, and so on.

A stress event to which each of the subjects is exposed during a corresponding one of the different stress states may include, but is not limited to, relaxation, being administered an examination, being informed of an upcoming procedure, being subject to the procedure, sleeping, walking or running a predetermined distance or time, deep breathing for a predetermined time, meditating for a predetermined time, or the like.

Alternately or additionally, the method 650 may further include storing age, height, weight, BMI, gender, and/or medical conditions for each of the subjects in the database. In some embodiments, the first stress measurements and the second stress measurements used in the calculation of the first median value and the second median value are filtered according to these criteria. E.g., the first stress measurements and the second stress measurements used in the calculation of the first median value and the second median value may be limited to first stress measurements and second stress measurements from a subset of the subjects, where each of the subset of the subjects may be similar to the first subject with respect to at least one of age, height, weight, BMI, gender, and/or medical conditions.

Alternately or additionally, the method 650 may further include storing orthogonal measurements for the subjects in the database. The orthogonal measurements may include at least one of heart rate and breathing rate for each of the subjects. In these and other embodiments, the comparison of the first stress measurement to the first median value may yield a first conclusion that is in conflict with a second conclusion yielded by the comparison of the second stress measurement to the second median value. For instance, one of the comparisons may indicate that the subject is more stressed than the other subjects, while the other comparison may indicate that the subject is less stressed than the other subjects. Accordingly, the method 650 may further include determining whether the first subject is stressed by resolving the conflict based on the orthogonal measurements, as already described above with respect to the database 205 of FIG. 2.

Figure 7:
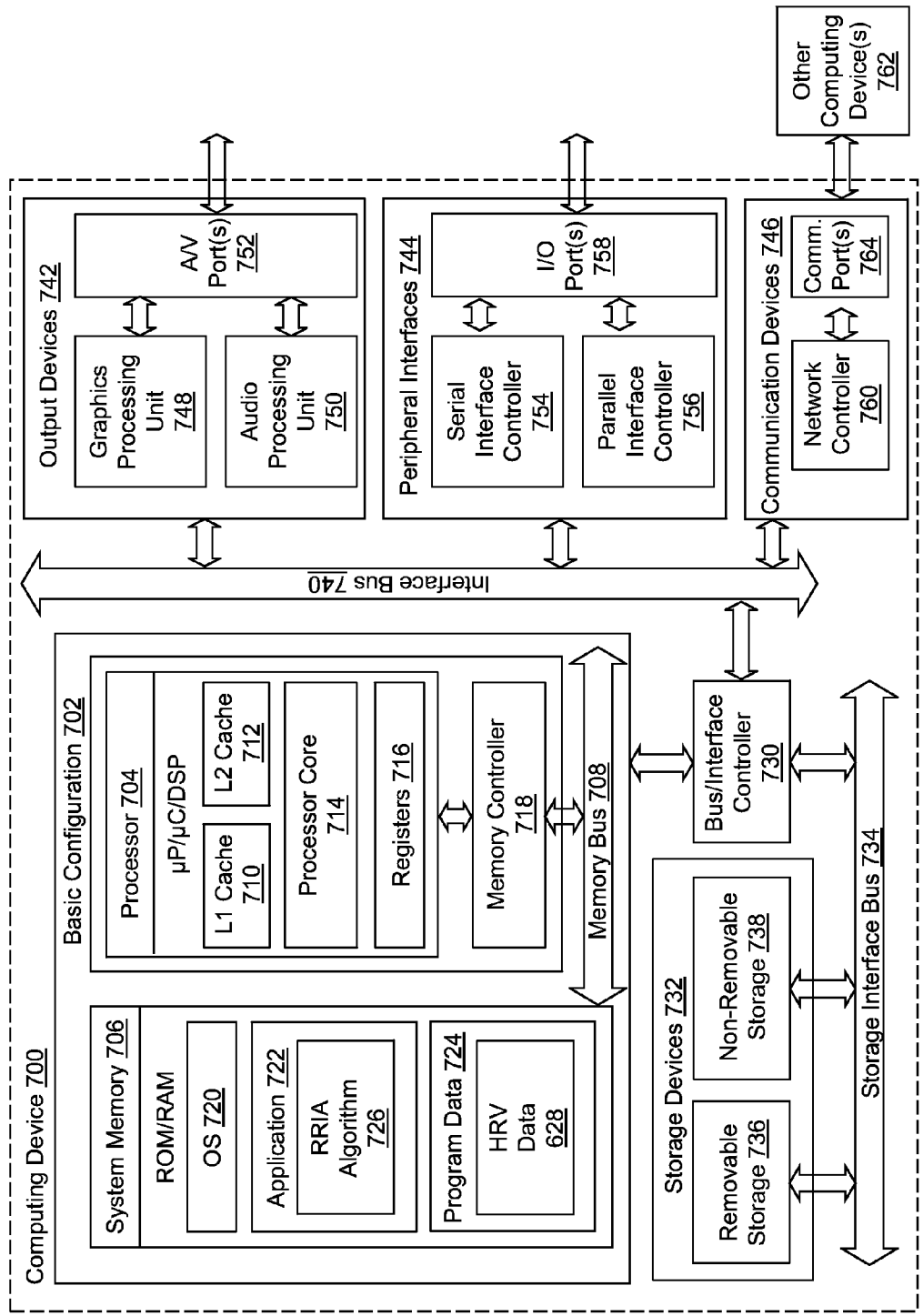
FIG. 7 is a block diagram illustrating an example computing device that is arranged for determining stress, all arranged in accordance with at least some embodiments described herein.

FIG. 7 is a block diagram illustrating an example computing device 700 that is arranged for determining stress, arranged in accordance with at least some embodiments described herein. The computing device 700 may correspond to the computing device 204 and/or may include or be connected to the database 205 of FIG. 2, for example. In a very basic configuration 702, the computing device 700 may include one or more processors 704 and a system memory 706. A memory bus 708 may be used for communicating between the processor 704 and the system memory 706.

Depending on the desired configuration, the processor 704 may be of any type including but not limited to a microprocessor (µP), a microcontroller (µC), a digital signal processor (DSP), or any combination thereof. The processor 704 may include one more levels of caching, such as a level one cache 710 and a level two cache 712, a processor core (or cores) 714, and registers 716. An example processor core 714 may include an arithmetic logic unit (ALU), a floating point unit (FPU), a digital signal processing core (DSP Core), or any combination thereof. An example memory controller 718 may also be used with the processor 704, or in some implementations the memory controller 718 may be an internal part of the processor 704. The processor 704 may be configured to perform one or more of the operations described herein by, for example, executing computer instructions or code loaded into the system memory 706 and/or by executing computer instructions or code line-by-line without using the system memory 706.

Depending on the desired configuration, the system memory 706 may be of any type including but not limited to volatile memory (such as Random Access Memory (RAM)), non-volatile memory (such as Read Only Memory (ROM), flash memory, etc.) or any combination thereof. The system memory 706 may include an operating system 720, one or more applications 722, and program data 724. The application 722 may include an RRIA algorithm 726 that is arranged to perform one or more of the operations associated with obtaining and processing a data signal including multiple consecutive RR intervals to determine stress of the subject as described herein, including one or more of the operations described with respect to FIG. 6A. Alternately or additionally, the application 722 may include an algorithm arranged to perform one or more of the operations described with respect to FIG. 6B. More generally, the application 722 may be executed by the processor 704 to cause the computing device 700 to perform the functions as described herein. The program data 724 may include HRV data 728 indicating the heart rate variability of the subject, which HRV data 728 may include an HRV histogram as is described herein. In some embodiments, the application 722 may be arranged to operate with the program data 724 on the operating system 720 such that stress of a subject may be determined based on the RRIA and/or according to other stress models.

The computing device 700 may have additional features or functionality, and additional interfaces to facilitate communications between the basic configuration 702 and other devices and interfaces. For example, a bus/interface controller 730 may be used to facilitate communications between the basic configuration 702 and one or more data storage devices 732 via a storage interface bus 734. The data storage devices 732 may be removable storage devices 736, non-removable storage devices 738, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer-readable instructions, data structures, program modules, or other data.

The system memory 706, the removable storage devices 736 and the non-removable storage devices 738 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by the computing device 700. Any such computer storage media may be part of the computing device 700.

The computing device 700 may also include an interface bus 740 for facilitating communication from various interface devices (e.g., output devices 742, peripheral interfaces 744, and/or communication devices 746) to the basic configuration 702 via the bus/interface controller 730. Example output devices 742 include a graphics processing unit 748 and an audio processing unit 750, which may be configured to communicate to various external devices such as a display or speakers via one or more A/V ports 752. Example peripheral interfaces 744 include a serial interface controller 754 or a parallel interface controller 756, which may be configured to communicate with external devices such as input devices (e.g., keyboard, mouse, pen, voice input device, touch input device, etc.) or other peripheral devices (e.g., printer, scanner, etc.) via one or more I/O ports 758. An example communication device 746 includes a network controller 760, which may be arranged to facilitate communications with one or more other computing devices 762 over a network communication link via one or more communication ports 764.

The network communication link may be one example of a communication media. Communication media may typically be embodied by computer-readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer-readable media as used herein may include both storage media and communication media.

The computing device 700 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. The computing device 700 may also be implemented as a personal computer including both laptop computer and non-laptop computer configurations.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed is:

1. A method of determining stress, the method comprising:
receiving a data signal including multiple consecutive RR intervals of a subject;
calculating heart rate variability (HRV) data for the subject from the data signal, wherein the HRV data includes a plurality of differences, each of the plurality of differences including a difference between a given one of the multiple consecutive RR intervals and an immediately preceding RR interval; and
calculating an RR integral average (RRIA) from the HRV data, the RRIA indicating a stress level of the subject.

2. The method of claim 1, wherein the HRV data comprises an HRV histogram and wherein the calculating the RRIA comprises calculating a point in the HRV histogram which divides the HRV histogram into two equal areas.

3. The method of claim 2, wherein the calculating the RRIA comprises calculating the RRIA according to the equation $$\int_0^{RRIA} f(x)dx = \int_{RRIA}^{\infty} f(x)dx,$$

where f(x) represents the HRV histogram.

4. The method of claim 1, further comprising weighting the RRIA with at least one of an average heart rate of the subject or a root mean square of successive differences (RMSSD) of the multiple consecutive RR intervals, wherein the weighting comprises at least one of:
calculating a heart rate-weighted RRIA according to the equation HR_RRIA=(RRIA /$HR_{avg}$) * C1, where HR_RRIA is the heart rate-weighted RRIA, $HR_{avg}$ is the average heart rate of the subject, and C1 is a constant; and
calculating an RMSSD-weighted HR_RRIA according to the equation RMSSD_HR_RRIA=HR_RRIA * RMSSD/C2, where RMSSD_HR_RRIA is the RMSSD-weighted HR_RRIA and C2 is a constant.

5. The method of claim 4, wherein $HR_{avg}$ is calculated over a time window having a predetermined length or over a window having a fixed number of the multiple consecutive RR intervals.

6. The method of claim 1, wherein:
the data signal includes a first data signal generated when the subject is in a non-stressed state,
the HRV data includes first HRV data, and
the RRIA comprises a first RRIA representing a baseline stress level of the subject; and
the method further comprises assessing a current stress level of the subject by:
receiving a second data signal including multiple consecutive RR intervals of a subject at a current time;
calculating second HRV data for the subject from the second data signal;
calculating a second RRIA from the second HRV data, the second RRIA indicating a current stress level of the subject;
comparing the first RRIA to the second RRIA or comparing a first value derived from the first RRIA to a second value derived from the second RRIA; and
determining whether the subject is in a stressed state based on the comparison, including:
determining that the subject is in a stressed state at the current time when at least one of: the second RRIA is less than the first RRIA or the second value is less than the first value; or
determining that the subject is in a non-stressed state at the current time when at least one of: the second RRIA is greater than the first RRIA or the second value is greater than the first value.

7. The method of claim 6, further comprising recommending a stress-reduction treatment for the subject to reduce the current stress level in response to determining that the subject is in a stressed state at the current time.

8. The method of claim 1, further comprising:
comparing:
the RRIA to a first median of a plurality of RRIAs for a plurality of subjects, each of the plurality of RRIAs corresponding to a different one of the plurality of subjects; or
a first value derived from the RRIA to a second median of a plurality of second values derived from the plurality of RRIAs, each of the plurality of second values corresponding to a different one of the plurality of RRIAs; and
determining whether the subject is in a stressed state based on the comparison, including:
determining that the subject is in a stressed state when at least one of: the RRIA is less than the first median or the first value is less than the second median; or
determining that the subject is in a non-stressed state when at least one of: the RRIA is greater than the first median or the first value is greater than the second median.

9. The method of claim 1, wherein the calculating the RRIA comprises calculating a median of the plurality of differences over a window of time having a predetermined length or over a window having a fixed number of the multiple consecutive RR intervals.

10. A system of determining stress, the system comprising
a cardiac sensor configured to generate a data signal including multiple consecutive RR intervals of a subject; and
a computing device communicatively coupled to the cardiac sensor, the computing device configured to:
receive the data signal;
calculate heart rate variability (HRV) data for the subject from the data signal, wherein the HRV data includes a plurality of differences, each of the plurality of differences including a difference between a given one of the multiple consecutive RR intervals and an immediately preceding RR interval; and
calculate an RR integral average (RRIA) from the HRV data, the RRIA indicating a stress level of the subject.

11. The system of claim 10, wherein the cardiac sensor comprises an electrocardiography device or a pulse oximeter.

12. The system of claim 10, wherein the computing device comprises a smartphone, a tablet computer, or a laptop computer.

13. The system of claim 10, further comprising a database communicatively coupled to the computing device and having stored thereon stress measurements for a plurality of subjects, including an RRIA, a heart rate-weighted RRIA (HR_RRIA), and/or a root mean square of successive differences-weighted HR_RRIA (RMSSD_HR_RRIA) for each of the plurality of subjects, wherein the computing device is further configured to compare the RRIA of the subject, an HR_RRIA of the subject, or an RMSSD_HR_RRIA of the subject to a corresponding median derived from the measurements in the database.

14. A method of determining stress, the method comprising:
- storing first stress measurements according to a first stress model for a plurality of subjects in a database;
- storing second stress measurements according to a second stress model for the plurality of subjects in the database;
- calculating a first median value from the first stress measurements and a second median value from the second stress measurements; and
- determining whether a first subject is stressed by respectively comparing a first stress measurement according to the first stress model for the first subject and a second stress measurement according to the second stress model for the first subject to the first median value and the second median value.

15. The method of claim 14, wherein:
- the first stress measurements and the second stress measurements include, for each of the plurality of subjects, a measurement according to the corresponding stress model for the corresponding subject in each of multiple different stress states;
- the first median value is calculated from the first stress measurements for a single one of the multiple different stress states; and
- the second median value is calculated from the second stress measurements for a single one of the multiple different stress states.

16. The method of claim 15, further comprising:
- calculating a plurality of different third median values, each of the plurality of different third median values being calculated from the first stress measurements for a different one of the multiple different stress states; and
- calculating a plurality of different fourth median values, each of the plurality of different fourth median values being calculated from the second stress measurements for a different one of the multiple different stress states.

17. The method of claim 15, wherein a stress event to which each of the plurality of subjects is exposed during a corresponding one of the multiple different stress states comprises relaxation, being administered an examination, being informed of an upcoming procedure, being subject to the procedure, sleeping, walking or running a predetermined distance or time, deep breathing for a predetermined time, or meditating for a predetermined time.

18. The method of claim 14, wherein the first stress model and the second stress model comprise two or more of: an RR integral average (RRIA) method, a heart rate-weighted RRIA (HR_RRIA) method, a root mean square of successive differences HR_RRIA (RMSSD_HR_RRIA) method, a Doppler Resistive Index (RI) method, or a power spectrum method.

19. The method of clam 14, further comprising storing age, height, weight, body mass index (BMI), gender, and/or medical conditions for each of the plurality of subjects in the database, wherein the first stress measurements and the second stress measurements used in the calculation of the first median value and the second median value are limited to first stress measurements and second stress measurements from a subset of the plurality of subjects, each of the subset of the plurality of subjects being similar to the first subject with respect to at least one of age, height, weight, BMI, gender, and/or medical conditions.

20. The method of claim 14, wherein:
- the method further comprises storing orthogonal measurements for the plurality of subjects in the database, the orthogonal measurements including at least one of heart rate and breathing rate for each of the plurality of subjects;
- the comparison of the first stress measurement to the first median value yields a first conclusion in conflict with a second conclusion yielded by the comparison of the second stress measurement to the second median value; and
- the method further comprises determining whether the first subject is stressed by resolving the conflict based on the orthogonal measurements.

* * * * *